United States Patent [19]

Farge et al.

[11] Patent Number: 4,503,220
[45] Date of Patent: Mar. 5, 1985

[54] CEPHALOSPORIN DERIVATIVES

[75] Inventors: Daniel Farge; Pierre L. Roy, both of Thiais; Claude Moutonnier, Le Plessis Robinson; Jean-Francois Peyronel, Palaiseau, all of France

[73] Assignee: Rhone-Poulenc Sante, Courbevoie, France

[21] Appl. No.: 408,674

[22] Filed: Aug. 16, 1982

[30] Foreign Application Priority Data

Aug. 17, 1981 [FR] France ................ 81 15806

[51] Int. Cl.³ ............... C07D 501/14; A61K 31/545
[52] U.S. Cl. ........................ 544/16; 544/22; 544/26; 544/27
[58] Field of Search ............ 544/16, 26, 27, 22; 424/246

[56] References Cited

U.S. PATENT DOCUMENTS

| | | | |
|---|---|---|---|
| 3,998,817 | 12/1976 | Fukumura et al. | 260/243 C |
| 4,043,991 | 8/1977 | Hamma et al. | 544/16 |
| 4,067,866 | 1/1978 | Foglio et al. | 260/239 A |
| 4,145,540 | 3/1979 | Ochiai et al. | 544/21 |
| 4,307,233 | 12/1981 | Farge et al. | 544/16 |
| 4,316,016 | 2/1982 | Walker et al. | 544/16 |
| 4,365,062 | 12/1982 | Farge et al. | 544/16 |

FOREIGN PATENT DOCUMENTS 1327102 8/1973 United Kingdom .
1459999 12/1976 United Kingdom .
2051062 1/1981 United Kingdom .

*Primary Examiner*—Nicholas S. Rizzo
*Attorney, Agent, or Firm*—Stevens, Davis, Miller & Mosher

[57] ABSTRACT

3-Vinylcephalosporin derivatives of the formula:

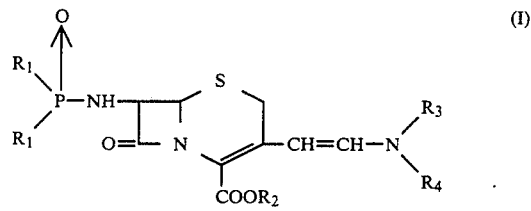

in which the symbols $R_1$ are phenyl radicals or radicals $-OZ_1$ (it being possible for $Z_1$ to be alkyl, 2,2,2-trichloroethyl or optionally substituted phenyl or benzyl, or for the radicals $Z_1$ to form an alkylene radical), $R_2$ is a radical which can be removed by an enzymatic method, or a protecting radical, and $R_3$ and $R_4$ are optionally substituted alkyl, or phenyl, or together form a saturated 5-membered or 6-membered heterocyclic ring optionally containing another hetero-atom, are new, crystallizable intermediates useful for the preparation of anti-bacterial cephalosporins.

13 Claims, No Drawings

CEPHALOSPORIN DERIVATIVES

The present invention relates to cephalosporin derivatives and their preparation and use.

Substituted 3-aminovinylcephalosporin derivatives which are useful as intermediates in the synthesis of anti-bacterial cephalosporins are described in Belgian Pat. No. 883,416 or U.S. Pat. No. 4,307,233.

The present invention provides a novel class of 3-vinyl-cephalosporins useful as intermediates in the preparation of anti-bacterial cephalosporins and of the formula:

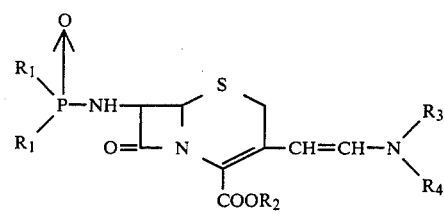

in which the substituent on the carbon atom in the 3-position of the bicyclooctene exhibits trans stereoisomerism, the symbols $R_1$ represent phenyl radicals or radicals —$OZ_1$, in which $Z_1$ is alkyl, 2,2,2,-trichloroethyl, phenyl or benzyl, the said phenyl and benzyl radicals being unsubstituted or substituted by a halogen atom or by an alkyl, alkoxy or nitro radical, or the two radicals $Z_1$ of the substituents $R_1$ together form an alkylene radical containing 2 or 3 carbon atoms, $R_2$ represents a radical which can easily be removed by an enzymatic method, of the formula:

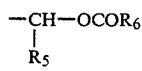

(in which $R_5$ represents a hydrogen atom or an alkyl radical and $R_6$ represents an alkyl or cyclohexyl radical), or a protecting radical, e.g. methoxymethyl, t-alkyl of 4 to 6 carbon atoms (e.g. t-butyl), t-alkenyl of 6 or 7 carbon atoms, t-alkynyl of 6 or 7 carbon atoms, benzhydryl, benzyl, p-nitrobenzyl, p-methoxybenzyl or 2,2,2-trichloroethyl, and the symbols $R_3$ and $R_4$, which are the same or different, represent alkyl radicals unsubstituted or substituted by an alkoxy or dialkylamino radical) or phenyl radicals, or together form, with the nitrogen atom to which they are attached, a saturated 5-membered or 6-membered heterocyclic ring optionally containing another hetero-atom chosen from nitrogen, oxygen and sulphur, and optionally substituted by an alkyl radical, e.g. pyrrolidino, piperidino or morpholino, it being understood that the said alkyl portions or radicals are linear or branched (unless otherwise stated) and contain 1 to 4 carbon atoms each.

Hereinafter, the trans stereoisomer will be designated by E and the cis stereoisomer will be designated by Z.

Among the radicals which may be represented by the group —$NR_3R_4$, the dimethylamino and piperidino radicals are especially preferred.

According to a feature of the invention, the compounds of the formula (I) in which $R_3$ and $R_4$ have the definitions given above can be obtained by reacting a compound, optionally prepared in situ, of the formula:

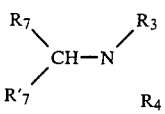

(in which $R_3$ and $R_4$ are as defined above and $R_7$ and $R'_7$, which are the same or different, represent groups of the formula:

in which $X_2$ is an oxygen atom and $R_8$ represents an alkyl or phenyl radical, or represent in one case a radical of formula (IV) (in which $X_2$ is oxygen or sulphur) and in the other case an amino radical of the formula:

in which $R_9$ and $R_{10}$ are defined in the same way as $R_3$ and $R_4$ in the formula (III), or alternatively represent in each case a radical of the general formula (V) with a cephalosporin of the formula:

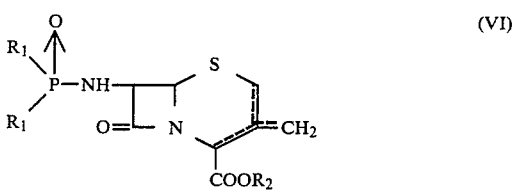

in which $R_1$ and $R_2$ are as defined above and which is in the form of a 3-methylbicyclooct-2-ene or 3-methylbicyclooct-3-ene or a 3-methylenebicyclooctane.

The reaction is generally carried out in an organic solvent, such as an amide (e.g. dimethylformamide, dimethylacetamide or hexamethylphosphorotriamide), a nitrile (e.g. acetonitrile), an ester (e.g. ethyl acetate), an ether (e.g. dioxane) or a chlorinated solvent (e.g. 1,2-dichloroethane), or alternatively in a mixture of such solvents, at a temperature of between 20° C. and the reflux temperature of the reaction mixture.

If a product of the formula (III) is chosen in which the radical (V) is different from —$NR_3R_4$, it is preferable to choose this product so that the amine $HNR_9R_{10}$ is more volatile than the amine $HNR_3R_4$.

The compounds of the formula (III) can be prepared in accordance with the methods described by H. BREDERECK et al., Chem. Ber. 101, 41 (1968), Chem. Ber. 101, 3058 (1968) and Chem. Ber. 106, 3725 (1973).

The cephalosporin derivatives of the formula (VI) can be prepared by applying the method described by A. MORIMOTO et al., J.C.S. Perkin I, 1109 (1980), starting from a halide of the general formula:

in which R₁ is as defined above and Hal represents a halogen atom, and a 7-aminocephalosporin of the formula:

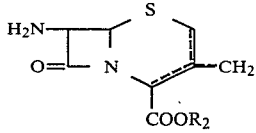

in which R₂ is as defined above, or by one of the methods mentioned below in the Examples.

The halide of the formula (VII) can be prepared by one of the methods described by K. SASSE, Methoden der Organischen Chemie (Methods of Organic Chemistry), Volume 12, part 2, page 274, Houben Weyl, Georg Thieme Verlag, Stuttgart (1964).

The 7-aminocephalosporins of the formula (VIII) can be obtained as described in Belgian Pat. No. 883,416.

The new compounds of the formula (I) are useful as intermediates for the preparation of the 3-thiovinylcephalosporins described in Belgian Pat. No. 883,416, which correspond to the general formula:

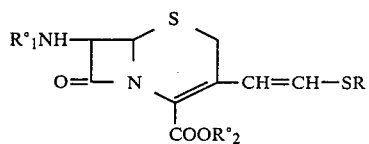

in which:

(α) the symbol R is chosen from amongst the following meanings:

(1) alkyl, L-2-amino-2-carboxyethyl or phenyl, (2) optionally N-oxidised pyrid-2-yl, pyrid-3-yl or pyrid-4-yl, (3) pyrimidin-2-yl, pyridazin-3-yl substituted in the 6-position (by an alkyl, methoxy, amino or acylamino radical) and optionally N-oxidised, or tetrazolo[4,5-b]pyridazin-6-yl, (4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, (a) by an alkyl radical containing 1 to 4 carbon atoms, which is unsubstituted or substituted by an alkoxy, alkylthio, phenyl, formyl, carbamoyl, alkylcarbamoyl, dialkylcarbamoyl, acyl, alkoxycarbonyl or thiazolidin-2-yl radical, (b) by an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, (c) by an alkyl radical containing 2 to 4 carbon atoms, which is substituted by hydroxyl, carbamoyloxy, acyloxy (the acyl part of which can be substituted by an amino, alkylamino or dialkylamino radical), alkylsulphinyl, alkylsulphonyl, amino, alkylamino, dialkylamino, sulphoamino, alkylsulphonylamino, sulphamoylamino, acylamino (the acyl part of which is optionally substituted by hydroxyl, amino, alkylamino or dialkylamino), alkoxycarbonylamino, ureido, alkylureido or dialkylureido, (d) by a radical corresponding to one of the general formulae:

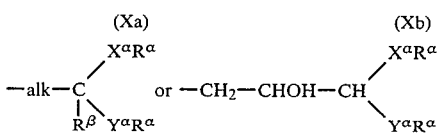

in which alk represents an alkylene radical containing 1 to 4 carbon atoms, $X^α$ and $Y^α$ are identical and represent oxygen or sulphur atoms and $R^α$ represents an alkyl radical, or alternatively $X^α$ and $Y^α$ are identical or different and represent oxygen or sulphur atoms and the radicals $R^α$ together form an alkylene radical containing 2 or 3 carbon atoms, and $R^β$ represents a hydrogen atom or an alkyl radical containing 1 to 3 carbon atoms, or (e) by an alkyl radical containing 2 to 5 carbon atoms, which is substituted by an alkoxyimino or hydroxyimino radical, (5) 1,4-dialkyl-5,6-dioxo-1,4,5,6-tetrahydro-1,2,4-triazine-3-yl, 1-alkyl-5,6-dioxo-1,4,5,6-tetrahydro-1,2,4-triazine-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl which is unsubstituted or substituted in the 3-position by alkoxycarbonyl, (7) (a) 1,3,4-thiadiazol-5-yl which is unsubstituted or substituted by an alkyl, trifluoromethyl, alkoxy or alkylthio radical, a hydroxyalkylthio radical, the alkyl part of which contains 2 to 4 carbon atoms, or an alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, and (b) 1,2,4-thiadiazol-5-yl substituted by an alkyl or alkoxy radical, (8) (a) 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, and (b) oxazol-2-yl or 4-alkyloxazol-2-yl, and (9) tetrazol-5-yl which is unsubstituted or substituted in the 1-position by (a) an alkyl radical containing 1 to 4 carbon atoms, which is unsubstituted or substituted by alkoxy, sulpho, carboxyl, formyl or sulphamoyl, (b) an alkyl radical containing 2 to 4 carbon atoms, which is substituted or hydroxyl, amino, alkylamino, dialkylamino, acylamino, carboxyalkylamino, sulphamoxylamino, sulphoamino, ureido, alkylureido or dialkylureido, (c) an alkyl radical containing 2 to 5 carbon atoms, which is substituted by hydroxyimino or alkoxyimino, (d) a phenyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, or (e) a radical of the general formula (Xa) in which $R^β$ represents a hydrogen atom, or a radical of the general formula (Xb), the symbol $R°_1$ represents a radical of the general formula:

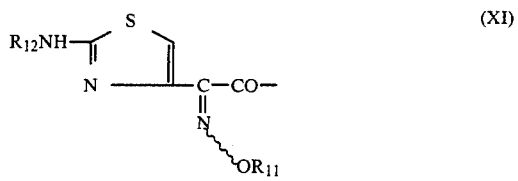

in which $R_{11}$ is hydrogen, alkyl, vinyl or cyanomethyl and $R_{12}$ represents a hydrogen atom, and the symbol $R°_2$ represents a hydrogen atom or a radical of the general formula (II), or alternatively (β) the symbol R represents an alkyl or phenyl radical, the symbol $R°_1$ represents 1°/an alkanoyl radical containing 1 to 8 carbon atoms, an alkanoyl radical containing 2 to 8 carbon atoms, which is substituted by chlorine or bromine atom, an acyl radical of the general formula:

[[in which each Q is H or methyl and Ar represents a thien-2-yl, thien-3-yl, furan-2-yl, furan-3-yl, pyrrol-2-yl or pyrrol-3-yl radical or a phenyl radical [optionally substituted by halogen atoms, hydroxyl radicals, alkyl radicals (containing 1 to 3 carbon atoms) or alkoxy radicals (containing 1 to 3 carbon atoms), at least one of which is located in the meta-position or para-position of the phenyl]]], an acyl radical of the general formula:

[[in which $X_1$ is oxygen or sulphur and Ar is defined as above, or Ar—$X_1$— represents pyrid-4-yl-thio]], an acyl radical corresponding to the general formula:

[[in which Ar is defined as above and B represents an amino radical [protected by a benzyloxycarbonyl, alkoxycarbonyl, cyclopentoxycarbonyl, cyclohexyloxycarbonyl, benzhydryloxycarbonyl, trityl or 2,2,2-trichloroethoxycarbonyl group], a sulpho radical, or a hydroxyl or carboxyl radical [optionally protected by esterification with, respectively, an alkanoic acid or an alcohol (containing 1 to 6 carbon atoms)]]] or a 5-aminoadipoyl radical [[in which the amino group is optionally protected by an alkanoyl radical (containing 1 to 3 carbon atoms and optionally substituted by a chlorine atom) and in which the carboxyl group is protected by a benzhydryl or 2,2,2-trichloroethyl group, a t-alkyl group (containing 4 to 6 carbon atoms) or a nitrobenzyl group]], or alternatively $R°_1NH$— is replaced by a cyclic imide group of a dicarboxylic acid, or 2°/an azidoacetyl or cyanoacetyl radical, a radical of the general formula (XII) in which Ar is phenyl [substituted by trifluoromethyl, cyano or nitro radicals, at least one of which is located in the meta-position or para-position], a radical of the general formula (XIV) [in which Ar is defined as above and B is amino, azido, cyano or carbamoyl], a (3-sydnone)-2-alkanoyl radical (the alkanoyl part of which contains 1 to 3 carbon atoms) or a radical of the general formula:

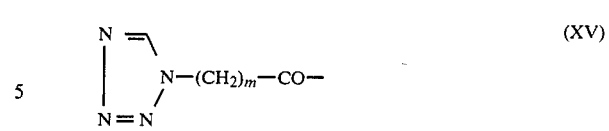

in which m is 0 to 2, and the symbol $R°_2$ is a protecting radical such as defined for $R_2$, or represents a hydrogen atom.

It is understood that in the products of the general formula (IX), the substituent in the 3-position of the bicyclooctene exhibits E/Z stereoisomerism, and that if $R°_1$ is a radical of the general formula (XI), it can be in the syn or anti form. The products of the general formula (IX) also exist as mixtures of these isomeric forms.

It is also understood that the alkyl or acyl portions or radicals are linear or branched (unless mentioned otherwise) and contain 1 to 4 carbon atoms.

The products of the general formula (IX) can be obtained from the products of the general formula (I) by the following procedure:

The products of the general formula:

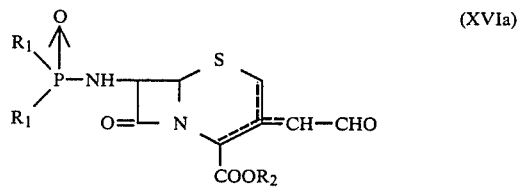

in which $R_1$ and $R_2$ are defined as above, and which is in the form of a 3-(2-oxoethyl)-bicyclooct-2-ene or 3-(2-oxoethyl)-bicyclooct-3-ene or a 3-oxoethylidenebicyclooctane, are prepared by hydrolysis, in an acid medium, of the enamine of the general formula (I) or a mixture of its isomers.

The reaction is generally carried out in an organic acid (e.g. formic acid or acetic acid) or a mineral acid (e.g. hydrochloric acid or sulphuric acid), in the presence or absence of a solvent, in an aqueous or organic medium, at a temperature of between −20° C. and the reflux temperature of the reaction mixture, and the product is then treated, if appropriate, with an inorganic base (an alkali metal bicarbonate) or an organic base (a tertiary amine or pyridine).

If the reaction is carried out in an organic medium, the hydrolysis is carried out by adding water to the reaction mixture.

If the reaction is carried out in the presence of a solvent, it is not necessary for the solvent to be miscible with the acid aqueous phase. Contact is then effected by vigorous stirring.

Amongst the solvents which can be used, there may be mentioned chlorinated solvents, ethyl acetate, tetrahydrofuran, acetonitrile, dimethylformamide and alcohols.

The products of the general formula:

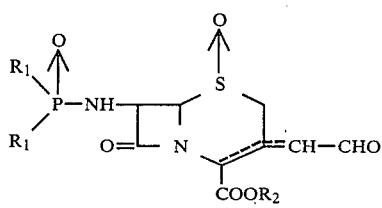

(XVIb)

in which $R_1$ and $R_2$ are defined as above, and which is in the form of a 3-(2-oxoethyl)-bicyclooct-2-ene or a 3-oxoethylidenebicyclooctane, can be obtained by oxidising the products of the general formula (XVIa) by applying the method described in German Patent Application No. 2,637,176.

The products of the general formula:

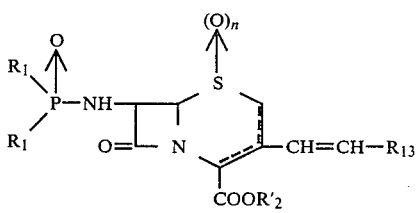

(XVII)

[in which $R_1$ is defined as above and $R'_2$ has the corresponding definition of $R_2$ or represents hydrogen, it being understood that if $n=0$, the product is in the form of a bicyclooct-2-ene or bicyclooct-3-ene, and if $n=1$, the product is in the form of a bicyclooct-2-ene, the substituent on the carbon atom in the 3-position of the bicyclooctene exhibits E/Z stereoisomerism and the symbol $R_{13}$ represents a halogen atom or a radical of the general formula:

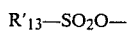  $R'_{13}-SO_2O-$ (XVIIIa)

or

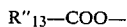  $R''_{13}-COO-$ (XVIIIb)

(in which formulae $R'_{13}$ represents an alkyl, trifluoromethyl or trichloromethyl radical or a phenyl radical which is unsubstituted or substituted by a halogen atom or by an alkyl or nitro radical, and $R''_{13}$ is defined in the same way as $R_{13}$ or represents an acylmethyl, 2-acylethyl, 2-acylpropyl, alkoxycarbonylmethyl, 2-alkoxycarbonylethyl or 2-alkoxycarbonylpropyl radical)] are then prepared by reacting a halogenating agent or an activated form of an acid $R'_{13}SO_3H$ or $R''_{13}COOH$, of the general formulae:

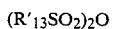  $(R'_{13}SO_2)_2O$ (XIXa)

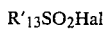  $R'_{13}SO_2Hal$ (XIXb)

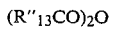  $(R''_{13}CO)_2O$ (XIXc)

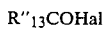  $R''_{13}COHal$ (XIXd)

[in these formulae, $R'_{13}$ and $R''_{13}$ are defined as above and Hal represents a halogen atom], with a product of the general formulae (XVIa) or (XVIb) or with a mixture of its isomers, this being followed, if appropriate, by reduction of the sulphoxide obtained and, if necessary, by removal of the protecting group of the acid group, if it is desired to obtain a product of the general formula (XVII) in which the acid group is free.

The reaction is generally carried out in the presence of a tertiary base of the type:

(XX)

in which X, Y and Z represent alkyl or phenyl radicals, or, if appropriate, two of them form a ring with the nitrogen atom to which they are attached (e.g. in the presence of triethylamine or N,N-dimethylaniline), in a chlorinated organic solvent (e.g. methylene chloride), in an ester (e.g. ethyl acetate), in an ether (e.g. dioxane or tetrahydrofuran), in an amide (e.g. dimethylacetamide, dimethylformamide or hexamethylphosphorotriamide), in acetonitrile or N-methylpyrrolidone or in a mixture of such solvents, or directly in a basic solvent, such as pyridine, or alternatively, if $R_{13}$ is other than a halogen atom, the reaction is carried out in an aqueous-organic medium, in the presence of an alkaline condensation agent (e.g. an alkali metal bicarbonate, sodium hydroxide or potassium hydroxide), at a temperature of between $-78°$ C. and the reflux temperature of the reaction mixture.

If appropriate, the reaction is carried out under nitrogen.

If it is desired to prepare a product of the general formula (XVII) in which $R_{13}$ is a halogen atom, the halogenating agents can be chosen from amongst halogen derivatives of phosphorus, in particular:

triaryl phosphite/halogen addition compounds, phosphorus trichloride, phosphorus oxychloride, phosphorus pentachloride, dichlorotriphenylphosphorane or catechyltrichlorophosphorane, if $R_{13}$ is a chlorine atom, or phosphorus tribromide, phosphorus oxybromide, phosphorus pentabromide or catechyltribromophosphorane, if $R_{13}$ is a bromine atom.

If phosphorus trichloride (or tribromide) is used, this reagent is reacted with a product of the general formula (XVIa).

The catechyltrichlorophosphorane or catechyltribromophosphorane, which can be prepared in situ, can be obtained in accordance with the method described by H. GROSS and U. KARSCH, J. Prakt. Chem., 29, 315 (1965).

The triaryl phosphite/halogen addition compounds, which can be formed in situ, are described by H. N. RYDON and B. L. TONGE, J. Chem. Soc., 3043 (1956), by J. MICHALSKI et al., J. Org. Chem., 45, 3122 (1980) or in Belgian Pat. No. 881,424, and can be prepared in accordance with the methods mentioned in these documents.

The halogen derivatives of the general formula (XVII) are prepared in an anhydrous medium.

The S-oxide can be reduced under the conditions described in German Patent Application No. 2,637,176.

The removal of the protecting groups of the carboxyl radical is carried out e.g.:

in the case of a t-butyl, p-methoxybenzyl or benzhydryl group: by treatment in an acid medium.

Preferably, trifluoroacetic acid is used, the reaction being carried out at a temperature of between 0° and 20° C., or alternatively anhydrous or aqueous formic acid, orthophosphoric or polyphosphoric acid or paratoluenesulphonic or methylsulphonic acid is used, in acetone or acetonitrile, at a temperature of between 20° C. and the reflux temperature of the reaction mixture.

In the case of the benzhydryl radical, the reaction can be carried out in the presence of anisole.

in the case of a methoxymethyl group: by treatment in a dilute acid medium, or in the case of a p-nitrobenzyl group: by reduction (in particular by treatment with zinc in acetic acid or by hydrogenolysis).

The products of the general formula (XVII) can then be treated in accordance with one or other of the following methods, in order to prepare the 3-thiovinyl-cephalosporins of the general formula (IX):

A/ A 7-aminocephalosporin of the general formula:

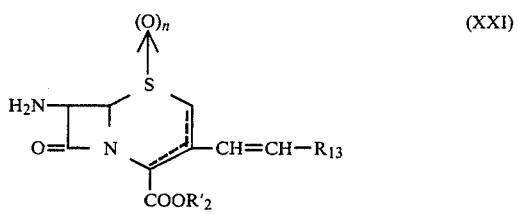

[in which n, $R'_2$ and $R_{13}$ are defined as above and the position of the double bond, and also the configuration of the substituent in the 3-position, are defined as for the general formula (XVII)] is prepared by removing the radical $(R_1)_2P(O)—$, or, if appropriate, simultaneously removing the protecting radicals $(R_1)_2P(O)—$ and $R'_2$, from a product of the general formula (XVII).

The removal of the radical $(R_1)_2P(O)—$ is carried out by any method which is known for unblocking phosphoryl protecting groups, e.g. according to Belgian Pat. No. 833,619, according to the method described by P. HAAKE et al., J. Amer. Chem. Soc. 95, 8073 (1973), if $(R_1)_2P(O)—$ is a diphenylphosphinoyl radical, or alternatively by reduction (in particular with zinc in acetic acid) if $R_1$ is a 2,2,2-trichloroethoxy or p-nitrobenzyloxy radical.

The products of the general formula (IX) can then be prepared in accordance with the methods described in Belgian Pat. No. 883,416.

B/ A thiol of the general formula:

R—SH  (XXII)

(or one of its alkali metal or alkaline earth metal salts) [in which formula R, which is defined as under (α) or (β) in the general formula (IX), is optionally protected] is reacted with a cephalosporin derivative of the general formula (XVII) (or a mixture of its isomers), this being followed, if appropriate, by reduction of the sulphoxide obtained and, if appropriate, by removal of the protecting radicals, in order to prepare a product of the general formula:

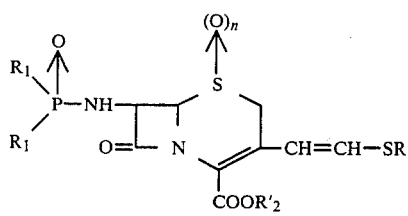

in which n and $R'_2$ are defined as above and R is defined as above.

If it is desired to obtain a product of the general formula (XXIII) in which R contains a formyl or acylalkyl radical, a thiol of the general formula (XXII) is used in which R is protected in the form of an acetal [as defined by the general formulae (Xa) and (Xb)]. P It is understood that if the radical R of the product of the general formula (XXII) is capable of interfering with the reaction, it is preferable to protect this group by any method which is in itself known and which does not affect the rest of the molecule.

The protection of the various amino, alkylamino, carboxyl or hydroxyl groups of R can be carried out e.g. as described in Belgian Pat. No. 883,416.

Furthermore, it is understood that if the radical R of the product of the general formula (XXII) contains a hydroxyl, sulpho, sulphinyl or sulphonyl radical, it is preferable to use a product of the general formula (XVII) in which n=0.

The reaction of the products of the general formulae (XXII) and (XVII) is generally carried out in the presence of a base, such as a pyridine or a tertiary organic base of the general formula (XX). Examples of bases used are diisopropylethylamine or diethylphenylamine.

If a salt of the thiol of the general formula (XXII) is used, it is not necessary to carry out the reaction in the presence of an organic base as defined above.

The reaction is advantageously carried out in an organic solvent, such as dimethylformamide, tetrahydrofuran, methanol or acetonitrile, or in a mixture of such solvents.

It is also possible to carry out the reaction in the presence of an alkali metal bicarbonate, in a solvent as defined above, if appropriate in the presence of water. The reaction is carried out at a temperature of between −20° C. and the reflux temperature of the reaction mixture, the chosen temperature varying according to the thiol employed. Likewise, the reaction time can vary from 5 minutes to 48 hours according to the thiol employed.

If appropriate, the reaction is carried out under nitrogen.

If necessary, the reduction of the oxide and the removal of the protecting radicals are carried out as described above or as described in Belgian Pat. No. 883,416.

A 7-aminocephalosporin of the general formula:

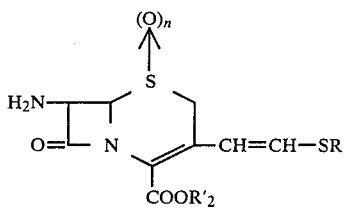

(XXIV)

in which n, R'$_2$ and R are defined as in the general formula (XXIII), is then prepared by removing the radical (R$_1$)$_2$P(O)—, or, if appropriate, simultaneously removing the radical (R$_1$)$_2$P(O)— and the other protecting radicals, from a product of the general formula (XXIII).

The reaction is carried out under conditions identical to those mentioned above for the preparation of the 7-aminocephalosporins of the general formula (XXI).

The products of the general formula (IX) can then be prepared in accordance with the methods described in Belgian Pat. No. 883,416.

The compounds according to the invention of formula I can be purified by physical methods, such as chromatography and especially crystallisation. It is an especially useful characteristic of the new compounds that they can be crystallized. For this reason, they are especially useful as synthesis intermediates.

The cephalosporin derivatives of the formula (IX) as defined under (α), and their pharmaceutically acceptable salts, which are described in Belgian Pat. No. 883,416, possess particularly valuable antibacterial properties.

The cephalosporin derivatives of the formula (IX) as defined under (β) are described in U.S. Pat. No. 4,065,620 for their antibacterial properties or as intermediates for the preparation of antibiotic substances.

Of particular value are the compounds of the formula (I) in which the symbols R$_1$ are radicals OZ$_1$ in which Z$_1$ is alkyl or phenyl, R$_2$ is a protecting radical chosen from benzhydryl, benzyl, p-nitrobenzyl, p-methoxybenzyl and 2,2,2-trichloroethyl, and the symbols R$_3$ and R$_4$, which are the same or different, represent alkyl radicals or together form, with the nitrogen atom to which they are attached, a saturated 5-membered or 6-membered heterocyclic ring optionally containing another heteroatom chosen from nitrogen, oxygen and sulphur, and optionally substituted by an alkyl radical; and, amongst these compounds, those which are more especially valuable are the compounds of the formula (I) in which the symbols R$_1$ are radicals OZ$_1$ in which Z$_1$ is alkyl containing 1 or 2 carbon atoms, or phenyl, R$_2$ is as defined above and R$_3$ and R$_4$, which are identical or different, represent alkyl radicals containing 1 or 2 carbon atoms each, or together form, with the nitrogen atom to which they are attached, a saturated 5-membered or 6-membered heterocyclic ring, and in particular:

7-dimethoxyphosphorylamino-3-(2-dimethylaminovinyl)-2-(4-methoxybenzyloxycarbonyl)-8-oxo-5-thia-1-azabicyclo[4.2.0]oct-2-ene, E isomer,
7-dimethoxyphosphorylamino-3-(2-dimethylaminovinyl)-2-(4-nitrobenzyloxycarbonyl)-8-oxo-5-thia-1-azabicyclo[4.2.0]oct-2-ene, E isomer,
7-dimethoxyphosphorylamino-2-(4-nitrobenzyloxycarbonyl)-8-oxo-3-(2-piperidinovinyl)-5-thia-1-azabicyclo[4.2.0]oct-2-ene, E isomer, and
2-benzhydryloxycarbonyl-7-diethoxyphosphorylamino-3-(2-dimethylaminovinyl)-8-oxo-5-thia-1-azabicyclo[4.2.0]oct-2-ene, E isomer.

The Examples which follow illustrate the invention.

In these Examples, the products are named according to the nomenclature of Chemical Abstracts. It is understood that all products according to the invention exhibit the stereochemistry given by the partial general formula:

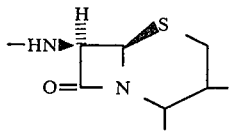

(XXV)

EXAMPLE 1

Bis-dimethylamino-t-butoxymethane (1.45 cc) is added to a solution of 2-benzyloxycarbonyl-7-dimethoxyphosphorylamino-3-methyl-8-oxo-5-thia-1-azabicyclo[4.2.0]oct-2-ene (2 g) in N,N-dimethylformamide (20 cc) at 80° C., and the reaction mixture is stirred for 5 minutes at 80° C. and diluted with ethyl acetate (100 cc). It is washed with distilled water (4×50 cc) and then with a saturated solution of sodium chloride (2×25 cc). The organic phase is dried over magnesium sulphate and then concentrated to dryness under reduced pressure (30 mm Hg; 4 kPa) at 30° C. This gives a red-brown crystalline solid (1.1 g) consisting mainly of 2-benzyloxycarbonyl-7-dimethoxyphosphorylamino-3-(2-dimethylaminovinyl)-8-oxo-5-thia-1-azabicyclo[4.2.0]oct-2-ene (E isomer). This product can be recrystallised from ethyl acetate to give pure 2-benzyloxycarbonyl-7-dimethoxyphosphorylamino-3-(2-dimethylaminovinyl)-8-oxo-5-thia-1-azabicyclo[4.2.0]oct-2-ene (E isomer) (0.5 g) in the form of yellow crystals (m.p.: 204°–205° C.).

2-Benzyloxycarbonyl-7-dimethoxyphosphorylamino-3-methyl-8-oxo-5-thia-1-azabicyclo[4.2.0]oct-2-ene can be prepared by analogy with the method described by A. MORIMOTO et al., J. C. S. Perkin I, 1109 (1980), by phosphorylating 7-amino-2-benzyloxycarbonyl-3-methyl-8-oxo-5-thia-1-azabicyclo[4.2.0]oct-2-ene with dimethoxyphosphoryl chloride. It is an orange crystalline solid, m.p.=126°–128° C.

7-Amino-2-benzyloxycarbonyl-3-methyl-8-oxo-5-thia-1-azabicyclo[4.2.0]oct-2-ene can be prepared in accordance with the method described in German Patent Application No. 2,709,292.

EXAMPLE 2

Bis-dimethylamino-t-butoxymethane (1.86 cc) is added to a solution of 7-dimethoxyphosphorylamino-2-(4-methoxybenzyloxycarbonyl)-3-methyl-8-oxo-5-thia-1-azabicyclo[4.2.0]oct-2-ene (3.5 g) in N,N-dimethylformamide (35 cc) at 80° C., and the reaction mixture is stirred for 8 minutes at 80° C. and diluted with ethyl acetate (250 cc) and distilled water (250 cc). The organic layer is washed with distilled water (3×200 cc) and then with a saturated solution of sodium chloride (200 cc), dried over magnesium sulphate and concentrated under reduced pressure (30 mm Hg; 4 kPa) at 30° C. to a residual volume of 50 cc. After 1 hour at 0° C., the crystals are filtered off, washed with ethyl acetate (3×20 cc) and with ethyl ether (2×10 cc) and then dried under 0.2 mm Hg (27 Pa). This gives 7-dimethoxyphosphorylamino-3-(2-dimethylaminovinyl)-2-(4-methoxybenzyloxycarbonyl)-8-oxo-5-thia-1-azabicyclo[4.2.0]oct-2-ene (E isomer) (1.6 g) in the form of an orange crystalline solid, m.p.=203°-205° C.

7-Dimethoxyphosphorylamino-2-(4-methoxybenzyloxycarbonyl)-3-methyl-8-oxo-5-thia-1-azabicyclo[4.2.0]oct-2-ene can be prepared by analogy with the method described by A. MORIMOTO et al., J. C. S. Perkin I, 1109 (1980), by phosphorylating 7-amino-2-(4-methoxybenzyloxycarbonyl)-3-methyl-8-oxo-5-thia-1-azabicyclo[4.2.0]oct-2-ene with dimethoxyphosphoryl chloride. It is in the form of white crystals, m.p.=137° C. (ethyl acetate).

7-Amino-2-(4-methoxybenzyloxycarbonyl)-3-methyl-8-oxo-5-thia-1-azabicyclo[4.2.0]oct-2-ene can be prepared in accordance with the method described in German Patent Application No. 2,243,242.

EXAMPLE 3

Bis-dimethylamino-t-butoxymethane (20 cc) is added to a solution of 7-dimethoxyphosphorylamino-3-methyl-2-(4-nitrobenzyloxycarbonyl)-8-oxo-5-thia-1-azabicyclo[4.2.0]oct-2-ene (22.9 g) in ethyl acetate (850 cc) at 45° C., and the reaction mixture is stirred for 20 hours at 45° C. and then for 2 hours at between 0° and 5° C. The crystals are filtered off, washed with ethyl acetate (3×40 cc) and then with isopropyl ether (3×50 cc) and dried. This give 7-dimethoxyphosphorylamino-3-(2-dimethylaminovinyl)-2-(4-nitrobenzyloxycarbonyl)-8-oxo-5-thia-1-azabicyclo[4.2.0]oct-2-ene (E isomer) (13.3 g) in the form of an orange crystalline powder, m.p.=242°-244° C. An analytically pure sample is obtained by recrystallisation from acetonitrile: yellow crystals, m.p.=252°-253° C.

7-Dimethoxyphosphorylamino-3-methyl-2-(4-nitrobenzyloxycarbonyl)-8-oxo-5-thia-1-azabicyclo[4.2.0]oct-2-ene can be prepared by applying the method described in South African Pat. No. 74/1,766.

EXAMPLE 4

By following the procedure of Example 3, but replacing the bis-dimethylamino-t-butoxymethane by tris-dimethylaminomethane (1.75 cc) and starting from 7-dimethoxyphosphorylamino-3-methyl-2-(4-nitrobenzyloxycarbonyl)-8-oxo-5-thia-1-azabicyclo[4.2.0]oct-2-ene (2.3 g), 7-dimethoxyphosphorylamino-3-(2-dimethylaminovinyl)-2-(4-nitrobenzyloxycarbonyl)-8-oxo-5-thia-1-azabicyclo[4.2.0]oct-2-ene (E isomer) (1.5 g) is obtained in the form of an orange crystalline powder, m.p.=236°-237° C. An analytically pure sample is obtained by recrystallisation from acetonitrile: yellow crystals, m.p.=252°-253° C.

EXAMPLE 5

Tripiperidinomethane (1.06 g) is added to a solution of 7-dimethoxyphosphorylamino-3-methyl-2-(4-nitrobenzyloxycarbonyl)-8-oxo-5-thia-1-azabicyclo[4.2.0]oct-2-ene (0.9 g) in ethyl acetate (40 cc) at 45° C., and the reaction mixture is stirred for 18 hours at 45° C. and diluted with ethyl acetate (20 cc). The organic solution is washed with distilled water (3×20 cc) and then with a saturated solution of sodium chloride (2×15 cc), dried over magnesium sulphate and concentrated to dryness under reduced pressure (30 mm Hg; 4 kPa) at 30° C. The residue obtained is recrystallised from ethyl acetate (5 cc), and 7-dimethoxyphosphorylamino-2-(4-nitrobenzyloxycarbonyl)-8-oxo-3-(2-piperidinovinyl)-5-thia-1-azabicyclo[4.2.0]oct-2-ene (E isomer) (0.2 g) is obtained in the form of an orange-yellow crystalline powder, m.p.=220°-221° C.

EXAMPLE 6 t-Butoxy-bis-dimethylaminomethane (6 cc) is added to a solution of 2-benzhydryloxycarbonyl-7-diethoxyphosphorylamino-3-methyl-8-oxo-5-thia-1-azabicyclo[4.2.0]oct-2-ene (10 g) in dry N,N-dimethylformamide (100 cc) at 80° C. After 12 minutes at 80° C., the reaction mixture is poured into ethyl acetate (400 cc) and washed with distilled water (5×250 cc). After drying over magnesium sulphate and evaporation of the solvent under reduced pressure (30 mm Hg; 4 kPa) at 30° C., 2-benzhydryloxycarbonyl-7-diethoxyphosphorylamino-3-(2-dimethylaminovinyl)-8-oxo-5-thia-1-azabicyclo[4.2.0]oct-2-ene (E isomer) (10.5 g) is obtained in the form of an orange crystalline solid. This product is purified by crystallisation from ethyl acetate (30 cc), and 2-benzhydryloxycarbonyl-7-diethoxyphosphorylamino-3-(2-dimethylaminovinyl)-8-oxo-5-thia-1-azabicyclo-[4.2.0]oct-2-ene (E isomer) (5.3 g) is obtained in the form of a yellow crystalline powder (m.p.=193°-194° C.).

Infra-red spectrum (CHBr$_3$), characteristic bands (cm$^{-1}$): 3370, 3320, 2800, 1760, 1680, 1610, 1530, 1230, 1010, 970, 750.

Proton NMR spectrum (350 MHz, CDCl$_3$, δ in ppm, J in Hz): 1.35 and 1.40 (2t, J≃7, 6H, —CH$_3$); 2.90 (s, 6H, —N(CH$_3$)$_2$); 3.08 and 3.18 (2d, J≃15, 2H, —S—CH$_2$—); 3.84 (t, J≃10, 1H,

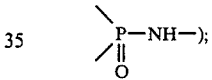

4.15 and 4.22 (2q, J≃7, 4H, —OCH$_2$—); 4.81 (dt, J≃4.5 and 10, 1H, —H in the 7-position); 5.08 (d, J≃4.5, 1H, —H in the 6-position); 6.53 and 6.78 (2d, J≃14, 2H, —CH=CH—N<); 6.88 (s, 1H, —COO— CH(C$_6$H$_5$)$_2$); 7.20 to 7.50 (m, 10H, aromatic protons).

2-Benzhydryloxycarbonyl-7-diethoxyphosphorylamino-3-methyl-8-oxo-5-thia-1-azabicyclo[4.2.0]oct-2-ene can be prepared in accordance with the method of A. Morimoto et al, J. C. S. Perkin I, 1109 (1980).

EXAMPLE 7

Bis-dimethylamino-t-butoxymethane (0.72 cc) is added to a suspension of 7-diethoxyphosphorylamino-3-methyl-2-(4-nitrobenzyloxycarbonyl)-8-oxo-5-thia-1-azabicyclo[4.2.0]oct-2-ene (1.2 g) in ethyl acetate (10 cc) at 35° C., the mixture is stirred for 20 hours at 35° C. and bis-dimethylamino-t-butoxymethane (0.72 cc) is then added in order to complete the reaction, the mixture being stirred for a further 2 hours at 35° C. The reaction mixture is cooled for 15 minutes with the aid of a bath of iced water. The crystals are filtered off, washed with ethyl acetate (5×5 cc) and dried. This gives 7-diethoxyphosphorylamino-3-(2-dimethylaminovinyl)-2-(4-nitrobenzyloxycarbonyl)-8-oxo-5-thia-1-azabicyclo[4.2.0]oct-2-ene (E isomer) (0.8 g) in the form of a yellow crystalline powder, m.p.=226°-227° C. An analytically pure sample is obtained by recrystallisation from acetonitrile: yellow crystals, m.p.=240°-241° C.

7-Diethoxyphosphorylamino-3-methyl-2-(4-nitrobenzyloxycarbonyl)-8-oxo-5-thia-1-azabicyclo[4.2.0]oct-2-ene can be prepared in accordance with the method of M. FUKUMURA et al., Chem. Pharm. Bull., 24, 3058 (1980).

EXAMPLE 8

Bis-dimethylamino-t-butoxymethane (0.72 cc) is added to a solution of 7-diethoxyphosphorylamino-3-methyl-2-(4-nitrobenzyloxycarbonyl)-8-oxo-5-thia-1-azabicyclo[4.2.0]oct-2-ene (1.2 g) in acetonitrile (7 cc) at 55° C., and the reaction mixture is stirred for 15 minutes at this temperature. It is cooled with an ice-water bath for 1 hour. The crystals which have formed are filtered off, washed with a mixture of acetonitrile and isopropyl ether (70/30 by volume) (5×3 cc) and dried under reduced pressure (0.2 mm Hg; 27 Pa). This gives 7-diethoxyphosphorylamino-3-(2-dimethylaminovinyl)-2-(4-nitrobenzyloxycarbonyl)-8-oxo-5-thia-1-azabicyclo[4.2.0]oct-2-ene (E isomer) (0.2 g) in the form of a yellow crystalline powder, m.p.=240°–241° C.

EXAMPLE 9

A solution of 7-diphenoxyphosphorylamino-3-methyl-8-oxo-2-(2,2,2-trichloroethoxycarbonyl)-5-thia-1-azabicyclo[4.2.0]oct-2-ene (2.02 g) and bis-dimethylamino-t-butoxymethane (1.035 cc) in dry dioxane (25 cc) is stirred at 60° C. for 1 hour and the reaction mixture is then diluted with ethyl acetate (100 cc) and distilled water (100 cc). The organic phase is washed with distilled water (3×100 cc) and then with a saturated solution of sodium chloride (100 cc) and dried over magnesium sulphate. The residue obtained after concentration to dryness under reduced pressure (30 mm Hg; 4 kPa) at 30° C. is chromatographed on a column (height=30 cm, diameter=2.2 cm) of silica gel (0.4–0.06 mm), elution being carried out under a pressure of 0.5 bar (50 kPa) with ethyl acetate, and 60 cc fractions being collected. Fractions 12 to 20, containing the pure product, are combined and evaporated to dryness under reduced pressure (30 mm Hg; 4 kPa) at 30° C. This gives a hard orange foam (1.4 g) consisting mainly of 3-(2-dimethylaminovinyl)-7-diphenoxyphosphorylamino-8-oxo-2-(2,2,2-trichloroethoxycarbonyl)-5-thia-1-azabicyclo[4.2.0]oct-2-ene (E isomer), which can be purified by crystallisation from a mixture of methylene chloride and ethyl ether (50/50 by volume) (20 cc). This gives pure 3-(2-dimethylaminovinyl)-7-diphenoxyphosphorylamino-8-oxo-2-(2,2,2-trichloroethoxycarbonyl)-5-thia-1-azabicyclo[4.2.0]oct-2-ene (E isomer) (0.7 g) in the form of yellow crystals, m.p.=120° C.

7-diphenoxyphosphorylamino-3-methyl-8-oxo-2-(2,2,2-trichloroethoxycarbonyl)-5-thia-1-azabicyclo[4.2.0]oct-2-ene can be prepared by analogy with the method described by A. MORIMOTO et al., J.C.S. Perkin I, 1109 (1980), by phosphorylating 7-amino-3-methyl-8-oxo-2-(2,2,2-trichloroethoxycarbonyl)-5-thia-1-azabicyclo[4.2.0]oct-2-ene with diphenoxyphosphoryl chloride.

7-Amino-3-methyl-8-oxo-2-(2,2,2-trichloroethoxycarbonyl)-5-thia-1-azabicyclo[4.2.0]oct-2-ene can be prepared in accordance with the method described in German Patent Application No. 2,243,242.

EXAMPLE 10

Bis-dimethylamino-t-butoxymethane (1.18 cc) is added to a solution of 2-benzhydryloxycarbonyl-7-diphenoxyphosphorylamino-3-methyl-8-oxo-5-thia-1-azabicyclo[4.2.0]oct-2-ene (2.32 g) in N,N-dimethylformamide (30 cc) at 80° C., and the reaction mixture is kept at 80° C. for 5 minutes and diluted with ethyl acetate (150 cc) and water (150 cc). The organic layer is washed with distilled water (5×100 cc) and with a saturated solution of sodium chloride (100 cc) and dried over magnesium sulphate. The residue obtained after concentration to dryness under reduced pressure (30 mm Hg; 4 kPa) at 30° C. is chromatographed on a column (height: 30 cm, diameter: 3.4 cm) of silica gel (0.04–0.06 mm), elution being carried out under a pressure of 0.5 bar (50 kPa) with a mixture of cyclohexane and ethyl acetate (50/50 by volume), and 60 cc fractions being collected. Fractions 17 to 25 are combined and evaporated under reduced pressure (30 mm Hg; 4 kPa) at 30° C. to a residual volume of 100 cc. The solution is stirred for 1 hour at 10° C. The crystals which have formed are filtered off, washed with a mixture of cyclohexane and ethyl acetate (50/50 by volume) (2×30 cc) and dried. This gives 2-benzhydryloxycarbonyl-3-(2-dimethylaminovinyl)-7-diphenoxyphosphorylamino-8-oxo-5-thia-1-azabicyclo[4.2.0]oct-2-ene (E isomer) (0.38 g), m.p.=226° C.

2-Benzhydryloxycarbonyl-7-diphenoxyphosphorylamino-3-methyl-8-oxo-5-thia-1-azabicyclo[4.2.0]oct-2-ene can be prepared by analogy with the method described by A. MORIMOTO et al., J. Chem. Soc. Perkin I, 1109 (1980), by phosphorylating 7-amino-3-methyl-8-oxo-5-thia-1-azabicyclo[4.2.0]oct-2-ene with diphenoxyphosphoryl chloride: the product obtained is in the form of a hard orange foam.

Infra-red spectrum (KBr), characteristic bands ($cm^{-1}$): 1780, 1720, 1590, 1490, 1450, 1210, 1180, 945, 755, 700. 7-Amino-3-methyl-8-oxo-5-thia-1-azabicyclo[4.2.0]oct-2-ene can be prepared in accordancd with the method described in German Patent Application No. 2,243,242.

REFERENCE EXAMPLE

The product of Example 6 can be used as follows:

A suspension of 2-benzhydryloxycarbonyl-7-diethoxyphosphorylamino-3-(2-dimethylaminovinyl)-8-oxo-5-thia-1-azabicyclo[4.2.0]oct-2-ene (E isomer) (5.1 g) in ethyl acetate (54 cc) is stirred for 1 hour 45 minutes with 1N hydrochloric acid (27 cc). The organic phase is decanted and washed with a saturated solution of sodium bicarbonate (60 cc) and a saturated solution of sodium chloride (60 cc) and then dried over magnesium sulphate and concentrated to dryness under reduced pressure (30 mm Hg; 4 kPa) at 35° C. This gives 2-benzhydryloxycarbonyl-7-diethoxyphosphorylamino-8-oxo-3-(2-oxoethyl)-5-thia-1-azabicyclo[4.2.0]oct-2-ene (4.9 g) in the form of a hard yellow foam.

Infra-red spectrum (CHBr$_3$), characteristic bands ($cm^{-1}$): 3380, 2730, 1780, 1720, 1490, 1440, 1245, 1020, 970, 755, 740.

Proton NMR spectrum (CDCl$_3$, 350 MHz, δ in ppm, J in Hz): 1.34 and 1.37 (2t, J=7, 2×3H, (CH$_3$CH$_2$O)$_2$PO—); 3.22 and 3.55 (2d, J=18, 2H, —SC$\overline{H}_2$—); 3.57 and 3.61 (2d, J=10.5, 2H, —CH$_2$CHO); 3.67 (t, J=10, 1H, —NH—); 4.07 to 4.23 (m, $\overline{4H}$, (CH$_3$CH$_2$O)$_2$PO—); 4.97 (d, J=4.5, 1H, H in the 6-position); 5.$\overline{17}$ (dt, J=4.5 and 10, 1H, H in the 7-position); 6.87 (s, 1H, —CO$_2$CH<); 7.2 to 7.5 (m, 10H, aromatic protons); 9.54 (s, 1H, —CHO).

Tosyl chloride (0.38 g) is added to a solution, cooled to −30° C., of 2-benzhydryloxycarbonyl-7-diethoxyphosphorylamino-8-oxo-3-(2-oxoethyl)-5-thia-1-azabicyclo[4.2.0]oct-2-ene (1.09 g) in ethyl acetate (12 cc), triethylamine (0.27 cc) is then added and the reaction mixture is kept at −30° C. for 7 hours and then at 20° C. for 16 hours. 1N Hydrochloric acid (5 cc) is added and the organic phase is washed successively with distilled water (5 cc), a saturated solution of sodium chloride (5 cc) and then distilled water (4×5 cc). The residue obtained after drying over magnesium sulphate and evaporation to dryness under reduced pressure (30 mm Hg; 4 kPa) at 35° C., is solidified by adding isopropyl ether (25 cc) and scratching. The solid is filtered off, washed with isopropyl ether (3×10 cc) and dried under reduced pressure (0.2 mm Hg; 27 Pa) at 20° C. This gives a mixture of the E and Z forms (90/10 by NMR) of 2-benzhydryloxycarbonyl-7-diethoxyphosphorylamino-8-oxo-3-(2-tosyloxyvinyl)-5-thia-1-azabicyclo[4.2.0]oct-2-ene (1.2 g) in the form of a cream-coloured solid.

Infra-red spectrum (CHBr$_3$), characteristic bands (cm$^{-1}$): 3380, 1780, 1720, 1630, 1590, 1490, 1370, 1190, 1175, 1070, 1050, 1015, 970, 755.

Proton NMR spectrum (CDCl$_3$, 350 MHz, δ in ppm, J in Hz):

for the E form: 1.3 to 1.42 (m, 6H, (CH$_3$CH$_2$O)$_2$-PO—); 2.46 (s, 3H, —CH$_3$ of the tosyl); 3.40 and 3.53 (2d, J=18, 2H, —SCH$_2$—); 3.51 (t, J=10.5, 1H, NH<); 4.05 to 4.25 (m, 4H, (CH$_3$CH$_2$O)$_2$PO—): 4.95 (d, J=5, 1H, H in the 6-position); 6.88 and 6.94 (2d, J=13, 2H, —CH=CHOSO$_2$—); 6.89 (s, 1H, —CO$_2$CH<); 7.2 to 7.50 (m, 12H, aromatic protons); 7.74 (d, J=7.5, 2H in the ortho-positions to the SO$_3$ of the tosyl).

for the Z form (characteristic signals): 2.50 (s, 3H, —CH$_3$ of the tosyl); 4.99 (d, J=5, 1H, H in the 6-position); 6.12 and 6.43 (2d, J=7, 2H, —CH=CH—OSO$_2$—); 6.95 (s, 1H, —CO$_2$CH<).

A solution of 2-benzhydryloxycarbonyl-7-diethoxyphosphorylamino-8-oxo-3-(2-tosyloxyvinyl)-5-thia-1-azabicyclo[4.2.0]oct-2-ene (90/10 mixture of the E and Z forms) (1.2 g) and the sodium salt of 4-(2,2-dimethoxyethyl)-5,6-dioxo-3-thioxo-perhydro-1,2,4-triazine (0.5 g) in dry N,N-dimethylformamide (12 cc) is stirred for 3 hours at 22° C. and then diluted with ethyl acetate (100 cc) and distilled water (30 cc). The organic phase is washed with distilled water (4×30 cc) and then dried over magnesium sulphate and concentrated to dryness under reduced pressure (30 mm Hg; 4 kPa) at 35° C. The residue obtained is crystallised from a mixture of methylene chloride and isopropyl ether (2/1 by volume) (15 cc). The crystals are filtered off, washed with a mixture of isopropyl ether and methylene chloride (1/1 by volume) (3×2 cc) and then with isopropyl ether (3×5 cc) and dried under reduced pressure (0.2 mm Hg; 27 Pa) at 20° C. This gives 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-diethoxyphosphorylamino-8-oxo-5-thia-1-azabicyclo[4.2.0]oct-2-ene (E form) (0.6 g) in the form of a white crystalline powder, m.p.=158°-160° C.

A mixture of 2-benzhydryloxycarbonyl-7-diethoxyphosphorylamino-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (E form) (0.4 g) and 85% strength orthophosphoric acid (4 cc) is stirred for 10 hours at 20° C. and then diluted with ethyl acetate (50 cc) and stirred for 15 minutes in a bath of iced water. The precipitate is filtered off, washed with ethyl acetate (5×10 cc) and dried under reduced pressure (0.2 mm Hg; 27 Pa) at 20° C. This gives 7-amino-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene phosphate (E form) (0.2 g) in the form of a cream-coloured solid.

Infra-red spectrum (KBr), characteristic bands (cm$^{-1}$): 3300-2000, 1780, 1715, 1585, 990.

An acetone solution of the mixed anhydride of p-toluenesulphonic acid and the syn isomer of 2-(2-tritylaminothiazol-4-yl)-2-methoxyiminoacetic acid [prepared by applying the method described by D. THJEODOROPOULOS and J. GAZOPOULOS, Peptide Synthesis, I, 27, 2091 (1962), starting from the triethylamine salt of the syn isomer of 2-(2-tritylaminothiazol-4-yl)-2-methoxyiminoacetic acid (2.72 g)] is added dropwise, with stirring, to a solution, cooled to 5° C., of the E isomer of 7-amino-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene phosphate (3 g) in dimethylacetamide (50 cc). The cooling bath is removed and the reaction mixture is stirred for 1 hour 30 minutes, diluted with water (500 cc) and filtered. The solid is washed with water (4×100 cc) and taken up in formic acid (100 cc), and the solution is diluted with water (20 cc) and stirred for 10 minutes at 50° C. It is concentrated to dryness at 30° C. under 0.05 mm Hg (7 Pa), the residue is taken up in acetone (3×50 cc), each mixture being concentrated to dryness, and then in acetone (50 cc), the resulting mixture is filtered and the solid is washed with acetone (3×50 cc) at 50° C. and dried in vacuo. The E form of the syn isomer of 7-[2-(2-aminothiazol-4-yl)-2-methoxyiminoacetamido]-2-carboxy-3-{2-[5,6-dioxo-4-formylmethyl-1,4,5,6-tetrahydro-1,2,4-triazin-3-yl]-thiovinyl}-8-oxo-5-thia-1-azabicyclo[4.2.0]oct-2-ene (2.4 g) is collected in the form of a cream-coloured powder, which is identical to the product obtained in Reference Example 12, variant 1a, of Belgian Patent No. 883,416.

We claim:

1. A 3-vinylcephalosporin of the formula:

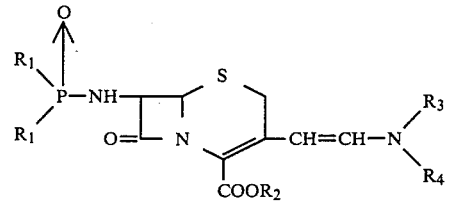

in which: the two symbols R$_1$ represent phenyl radicals or radicals —OZ$_1$, in which Z$_1$ is alkyl, 2,2,2-trichloroethyl, phenyl or benzyl, the said phenyl and benzyl radicals being unsubstituted or substituted by a halogen atom or by an alkyl, alkoxy or nitro radical, or the two radicals Z$_1$ of the substituents R$_1$ together form an alkylene radical of 2 or 3 carbon atoms; R$_2$ represents a radical of the formula:

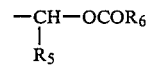

(in which R$_5$ represents a hydrogen atom or an alkyl radical and R$_6$ represents an alkyl or cyclohexyl radical), or a protecting radical; and R$_3$ and R$_4$, which are the same or different, represent alkyl radicals (unsubstituted or substituted by an alkoxy or dialkylamino radical) or phenyl radicals, or together form, with the nitrogen atom to which they are attached, a heterocyclic ring chosen from pyrrolidino, piperidino and morpholino, it being understood that the aforesaid alkyl portions or radicals are linear or branched and contain 1 to 4 carbon atoms each, and that the substituent in the 3-position of the bicyclooctene exhibits E stereoisomerism.

2. A 3-vinylcephalosporin according to claim 1, in which the symbols $R_1$ represent radicals $—OZ_1$ in which $Z_1$ is alkyl or phenyl, $R_2$ is a protecting radical chosen from benzhydryl, benzyl, p-nitrobenzyl, p-methoxybenzyl and 2,2,2-trichloroethyl, and $R_3$ and $R_4$, which are the same or different, represent alkyl radicals or together form, with the nitrogen atom to which they are attached, a heterocyclic ring chosen from pyrrolidino, piperidino and morpholino, it being understood that the said alkyl portions or radicals are linear or branched and contain 1 to 4 carbon atoms each, and that the substituent in the 3-position of the bicyclooctene exhibits E stereoisomerism.

3. A 3-vinylcephalosporin according to claim 2, in which the symbols $R_1$ represent radicals $—OZ_1$ in which $Z_1$ is an alkyl radical of 1 or 2 carbon atoms, or a phenyl radical, $R_2$ is as defined in claim 18, and $R_3$ and $R_4$, which are identical or different, represent alkyl radicals containing 1 or 2 carbon atoms each, or together form, with the nitrogen atom to which they are attached a heterocyclic ring chosen from pyrrlidino, piperidino, and morpholino, and in which the substituent in the 3-position of the bicyclooctene exhibits E stereoisomerism.

4. A 3-vinylcephalosporin according to claim 1 in crystalline form.

5. A 3-vinylcephalosporin according to claim 1, in which $R_2$ represents a protecting radical chosen from methoxymethyl, t-alkyl containing 4 to 6 carbon atoms, t-alkenyl containing 6 or 7 carbon atoms, t-alkynyl containing 6 or 7 carbon atoms, benzhydryl, benzyl, p-nitrobenzyl, p-methoxybenzyl and 2,2,2-trichloroethyl.

6. A 3-vinylcephalosporin according to claim 1 which is 2-benzyloxycarbonyl-7-dimethoxyphosphorylamino-3-(2-dimethylaminovinyl)-8-oxo-5-thia-1-azabicyclo[4.2.0]oct-2-ene (E isomer).

7. A 3-vinylcephalosporin according to claim 1 which is 7-dimethoxyphosphorylamino-3-(2-dimethylaminovinyl)-2-(4-methoxybenzyloxycarbonyl)-8-oxo-5-thia-1-azabicyclo[4.2.0]oct-2-ene (E isomer).

8. A 3-vinylcephalosporin according to claim 1 which is 7-dimethoxyphosphorylamino-3-(2-dimethylaminovinyl)-2-(4-nitrobenzyloxycarbonyl)-8-oxo-5-thia-1-azabicyclo[4.2.0]oct-2-ene (E isomer).

9. A 3-vinylcephalosporin according to claim 1 which is 7-dimethoxyphosphorylamino-2-(4-nitrobenzyloxycarbonyl)-8-oxo-3-(2-piperidinovinyl)-5-thia-1-azabicyclo[4.2.0]oct-2-ene (E isomer).

10. A 3-vinylcephalosporin according to claim 1 which is 2-benzhydryloxycarbonyl-7-diethoxyphosphorylamino-3-(2-dimethylaminovinyl)-8-oxo-5-thia-1-azabicyclo[4.2.0]oct-2-ene (E isomer).

11. A 3-vinylcephalosporin according to claim 1 which is 7-diethoxyphosphorylamino-3-(2-dimethylaminovinyl)-2-(4-nitrobenzyloxycarbonyl)-8-oxo-5-thia-1-azabicyclo[4.2.0]oct-2-ene (E isomer).

12. A 3-vinylcephalosporin according to claim 1 which is 3-(2-dimethylaminovinyl)-7-diphenoxyphosphorylamino-8-oxo-2-(2,2,2-trichloroethoxycarbonyl)-5-thia-1-azabicyclo[4.2.0]oct-2-ene (E isomer).

13. A 3-vinylcephalosporin according to claim 1 which is 2-benzhydryloxycarbonyl-3-(2-dimethylaminovinyl)-7-diphenoxyphosphorylamino-8-oxo-5-thia-1-aza-bicyclo[4.2.0]oct-2-ene (E isomer).

* * * * *